US011402380B2

(12) United States Patent
Spearman et al.

(10) Patent No.: US 11,402,380 B2
(45) Date of Patent: Aug. 2, 2022

(54) ASSAYS FOR DETECTING ANTIBODIES CAPABLE OF MEDIATING ANTIBODY-DEPENDENT CELL-MEDIATED CYTOTOXICITY

(71) Applicant: Emory University, Atlanta, GA (US)

(72) Inventors: Paul Spearman, Cincinnati, OH (US); Karnail Singh, Mason, OH (US); Xuemin Chen, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/258,484

(22) Filed: Jan. 25, 2019

(65) Prior Publication Data
US 2019/0227077 A1 Jul. 25, 2019

Related U.S. Application Data

(60) Provisional application No. 62/621,637, filed on Jan. 25, 2018.

(51) Int. Cl.
G01N 33/564 (2006.01)
G01N 33/52 (2006.01)
(Continued)

(52) U.S. Cl.
CPC ..... *G01N 33/56983* (2013.01); *C07K 14/005* (2013.01); *C07K 16/10* (2013.01); *C12N 5/0646* (2013.01); *C12N 15/62* (2013.01); *C12N 15/85* (2013.01); *C12Q 1/66* (2013.01); *G01N 33/52* (2013.01); *G01N 33/564* (2013.01); *G01N 33/577* (2013.01); *G01N 33/6854* (2013.01);
(Continued)

(58) Field of Classification Search
CPC .. G01N 33/6854; G01N 33/52; G01N 33/564; G01N 33/56983; G01N 33/577; C07K 14/08; C07K 2317/732; C12N 5/0646
See application file for complete search history.

(56) References Cited

U.S. PATENT DOCUMENTS 5,821,337 A 10/1998 Carter
6,737,056 B1 5/2004 Presta
(Continued)

FOREIGN PATENT DOCUMENTS

WO 2016077789 5/2016

OTHER PUBLICATIONS

Larson et al. An Automated DELFIA ADCC Assay Method using a CD16.NK-92 Cell Line (BioTek Instruments, Inc. Application Note , 2013).*

(Continued)

*Primary Examiner* — Gailene Gabel
(74) *Attorney, Agent, or Firm* — Emory Patent Group

(57) ABSTRACT

This disclosure relates to assays for detecting activating antibodies in a sample that are capable of antibody-dependent cell-mediated cytotoxicity. In certain embodiments, this disclosure relates to target cells comprising an antigen on the exterior of the cells and a luciferase inside the cells. In certain embodiments, the antigen is an Ebola-virus glycoprotein. In certain embodiments, this disclosure relates to detecting changes in chemiluminescence of the luciferase as an indication of activating antibodies in a sample capable of cell lysis when mixed with effector cells.

16 Claims, 4 Drawing Sheets

Figure 1:
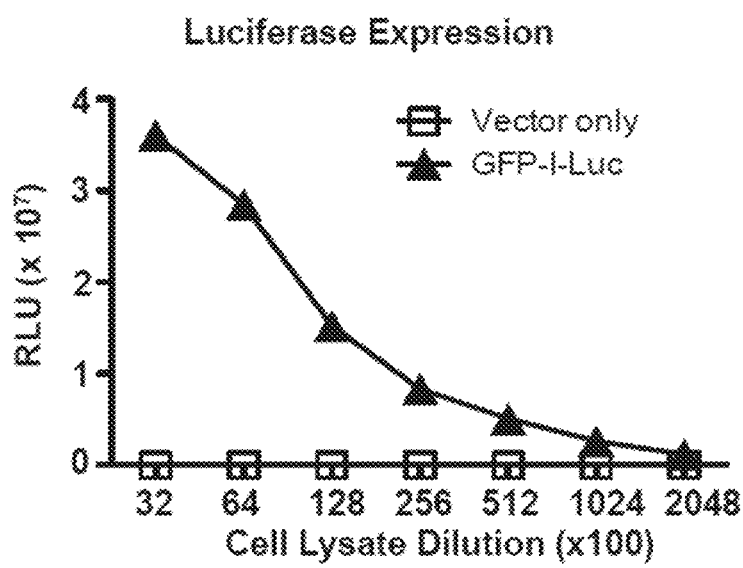
Figure 2:
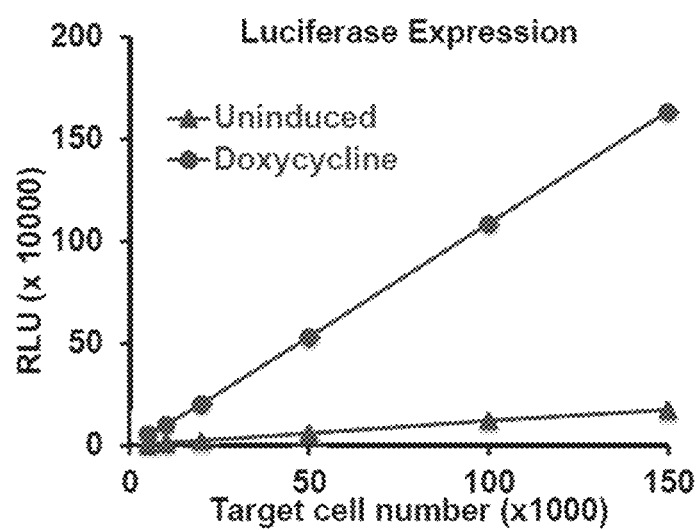

Specification includes a Sequence Listing.

(51) Int. Cl.

| | |
|---|---|
| C07K 14/08 | (2006.01) |
| G01N 33/569 | (2006.01) |
| G01N 33/68 | (2006.01) |
| C12N 5/0783 | (2010.01) |
| C12N 15/62 | (2006.01) |
| C12N 15/85 | (2006.01) |
| G01N 33/577 | (2006.01) |
| C07K 16/10 | (2006.01) |
| C07K 14/005 | (2006.01) |
| C12Q 1/66 | (2006.01) |
| C07K 16/28 | (2006.01) |

(52) U.S. Cl.
CPC .......... C07K 14/08 (2013.01); C07K 16/2803 (2013.01); C07K 2317/732 (2013.01); C07K 2317/76 (2013.01); C12N 2760/14122 (2013.01)

(56) References Cited

U.S. PATENT DOCUMENTS

| | | | |
|---|---|---|---|
| 2004/0092472 A1 | 5/2004 | Krieg | |
| 2009/0208500 A1 | 8/2009 | Joly | |
| 2010/0080825 A1* | 4/2010 | Kawaoka | C07K 14/005 424/204.1 |
| 2016/0131650 A1 | 5/2016 | Zafari | |
| 2018/0237503 A1* | 8/2018 | Takada | C12N 5/10 |

OTHER PUBLICATIONS

Parekh et al. Development and validation of an antibody-dependent cell-mediated cytotoxicity-reporter gene assay. mAbs 4 (3): 310-318 (2012).*

Singh et al. A Novel Ebola Virus Antibody-Dependent Cell-Mediated Cytotoxicity (Ebola ADCC) Assay. J Immunol Methods 460: 10-16 (Sep. 2018).*

Alpert et al. A Novel Assay for Antibody-Dependent Cell-Mediated Cytotoxicity against HIV-1- or SIV-Infected Cells Reveals Incomplete Overlap with Antibodies Measured by Neutralization and Binding Assays, Journal of Virology, 2012, 12039-12052.

Binyamin et al. Blocking NK Cell Inhibitory Self-Recognition Promotes Antibody-Dependent Cellular Cytotoxicity in a Model of Anti-Lymphoma Therapy, J Immunol. 2008, 180(9): 6392-6401.

Bonsignori et al. Antibody-Dependent Cellular Cytotoxicity-Mediating Antibodies from an HIV-1 Vaccine Efficacy Trial Target Multiple Epitopes and Preferentially Use the VH1 Gene Family, Journal of Virology, 2012, 11521-11532.

Kuipers, Use of ADCC Reporter Bioassays in Influenza Vaccine Development, Janssen Pharmaceuticals, Webinar 2016.

Larson, An Automated DELFIA ADCC Assay Method using a CD16.NK-92 Cell Line, BioTek, Application Note, 2013.

Parekh et al. Development and validation of an antibody-dependent cell-mediated cytotoxicity-reporter gene assay, mAbs, 2012, 4:3, 310-318.

Perussia et al. Assays for Antibody-Dependent Cell-Mediated Cytotoxicity (ADCC) and Reverse ADCC (Redirected Cytotoxicity) in Human Natural Killer Cells, Methods in Molecular Biology, 2000, vol. 121: Natural Killer Cell Protocols: Cellular and Molecular Methods, Chapter 16, 179-192.

Promega, ADCC Reporter BioAssay Core Kit, Technical Manual, TM383, 2016.

Quick et al. Real-time, portable genome sequencing for Ebola surveillance, Nature, 2016, 530(7589):228-232.

Singh et al. A novel Ebola virus antibody-dependent cell-mediated cytotoxicity (Ebola ADCC) assay, Journal of Immunological Methods, 2018, 460, 0-16.

Warfield et al. Ebola Virus-Like Particle-Based Vaccine Protects Nonhuman Primates against Lethal Ebola Virus Challenge, J Infect Dis, 2007, 196 Suppl 2:S430-7.

Chin et al. Pseudoparticle Neutralization Assay for Detecting Ebola-Neutralizing Antibodies in Biosafety Level 2 Settings, Clinical Chemistry 61:6, 885-888 (2015).

Corti et al. Protective monotherapy against lethal Ebola virus infection by a potently neutralizing antibody,Science. 2016, 351(6279):1339-42.

Li et al. An Ebola Virus-Like Particle-Based Reporter System Enables Evaluation of Antiviral Drugs In Vivo under Non-Biosafety Level 4 Conditions, J Virol, 2016, 90:8720-8728.

Liu et al. Antibody-dependent-cellularcytotoxicity-inducing antibodies significantly affect the post exposure treatment of Ebola virus infection, Sci Rep. 2017, 7:45552.

* cited by examiner

ASSAYS FOR DETECTING ANTIBODIES CAPABLE OF MEDIATING ANTIBODY-DEPENDENT CELL-MEDIATED CYTOTOXICITY

CROSS-REFERENCE TO RELATED APPLICATIONS

This application claims the benefit of U.S. Provisional Application No. 62/621,637 filed Jan. 25, 2018. The entirety of this application is hereby incorporated by reference for all purposes.

STATEMENT REGARDING FEDERALLY FUNDED RESEARCH

This invention was made with government support under HHSN272201300018I awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 16164US_ST25.txt. The text file is 15 KB, was created on Jan. 25, 2019, and is being submitted electronically via EFS-Web.

BACKGROUND

Ebolaviruses are filamentous, negative-strand RNA viruses belonging to the Filoviridae family. There are five known species of the Ebola-viruses; Zaire ebolavirus (EBOV), Sudan ebolavirus (SUDV), Bundibugyo ebolavirus (BDBV), Tai-forest ebolavirus (TAFV) and Reston ebolavirus (RESTV). The first four of these cause Ebola virus disease (EVD) in humans. Ebolavirus structure consists of an inner nucleocapsid made up of nucleoprotein (NP) and containing the viral RNA, along with RNA polymerase L, transcription factor VP30 and cofactor VP35. The viral nucleocapsid is surrounded by a lipid bilayer that contains the envelope protein spikes of glycoprotein (GP). Between the viral envelope and nucleocapsid are the matrix proteins VP40 and VP24. GP is a relevant target of both neutralizing and non-neutralizing antibodies that can protect against EVD.

Data from infected humans and from the non-human primate model of EVD indicate that fatal outcomes are generally associated with suppressed humoral and cell mediated immune responses, while survivors of EVD mount effective humoral and cell mediated immune responses against Ebola viral antigens. In support of antibody-mediated protection, administration of anti-Ebola GP antibodies has been shown to prevent the development of fatal disease in Ebola-infected non-human primates (NHP) even when administered post-infection. The anti-Ebola GP monoclonal antibody cocktail, ZMapp, was administered to some EVD patients after the onset of the clinical symptoms of the disease. However, assays to evaluate protective responses against Ebola are needed.

Quick et al. report genome sequencing for Ebola surveillance. Nature 530, 228-232, (2016). U.S. Patent Application Publication No. 2016/0131650 reports, Ebola test kits.

Larson report an automated DELFIA ADCC assay method using a CD16 NK-92 cell line. Application Notes, Cell-Based Assays, Biotherapeutics, Automation and Liquid Handling. BioTek® 2013. See also Perussia et al. (1999) Assays for Antibody-Dependent Cell-Mediated Cytotoxicity (ADCC) and Reverse ADCC (Redirected Cytotoxicity) in Human Natural Killer Cells. In: Campbell K. S., Colonna M. (eds) Natural Killer Cell Protocols. Methods in Molecular Biology, vol 121. Humana Press. See also U.S. Patent Application Publication 2009/0208500 (Joly et al.) and U.S. Pat. No. 6,737,056 (Presta) and U.S. Pat. No. 5,821,337 (Carter et al.).

References cited herein are not an admission of prior art.

SUMMARY

This disclosure relates to assays for detecting activating antibodies in a sample that are capable of mediating antibody-dependent cell-mediated cytotoxicity (ADCC). In certain embodiments, this disclosure relates to target cells comprising an antigen on the exterior of the cells and a luciferase inside the cells. In certain embodiments, the antigen is an Ebola-virus glycoprotein. In certain embodiments, this disclosure relates to detecting changes in chemiluminescence as an indication of activating antibodies in a sample capable of cell lysis when mixed with effector cells.

In certain embodiments, this disclosure relates to methods comprising expressing a luciferase and expressing an antigen such as a viral protein or glycoprotein in target cells, mixing the target cells with effector cells, purifying the cells and wherein, upon cell lysis, the luciferase is released into the surrounding media such that luciferase is capable of interacting with a luciferin resulting in a chemiluminescent signal. The chemiluminescent signal may be measured and correlated with the amount of target cell lysis by effector cells. In certain embodiments, detecting the presence or absence of a signal or a measured signal is compared to a control sample, e.g., a similarly performed assay with a control antibody with or without the function of inducing antibody-dependent cell-mediated cytotoxicity or a control sample that does not contain an antibody. In certain embodiments, the control sample comprises an antibody that binds the viral antigen and does not cause target cell lysis. In certain embodiments, the viral protein is an Ebola-virus protein.

In certain embodiments, this disclosure relates to methods comprising: a) mixing a sample suspected of containing an activating antibody with target cells and effector cells, wherein the target cells comprise a surface protein and a luciferase inside the target cell, b) incubating the sample for a period of time; c) centrifuging the sample providing a supernate and a cell pellet having target cells; and d) mixing the target cells or cell lysate thereof with a luciferin and detecting or measuring a chemiluminescent signal.

In certain embodiments, this disclosure relates to methods for detecting effector cell activating antibodies in a sample comprising: a) mixing a sample suspected of containing an activating antibody with target cells and effector cells, wherein the target cells comprise a surface protein and a luciferase inside the target cells, b) incubating the sample for a period of time; c) mixing the target cells or cell lysate thereof with a luciferin and detecting or measuring a chemiluminescent signal and d) correlating the chemiluminescent signal to a presence, absence, or quantity of cell activating antibodies in the sample.

In certain embodiments, this disclosure relates to methods for detecting effector cell activating antibodies in a sample comprising: a) mixing a sample suspected of containing an activating antibody with target cells and effector cells, wherein the target cells comprise a surface protein and a luciferase inside the target cells, b) incubating the sample for a period of time; c) centrifuging the sample providing a pellet comprising cells and a supernate comprising a liquid sample; d) purifying the pellet of cells from the supernate and lysing the cells in the pellet providing cell lysate; f) mixing the cell lysate with a luciferin and detecting or measuring a chemiluminescent signal of the cell lysate with the luciferin; and d) correlating the chemiluminescent signal to a presence, absence, or quantity of cell activating antibodies in the sample.

In certain embodiments, detecting the absence of a chemiluminescent signal at the time point compared to a control sample is an indication that the sample contained an activating antibody capable of antibody-dependent cell-mediated cytotoxicity. In certain embodiments, measuring a decreased chemiluminescent signal at the time point compared to a control sample is an indication that the sample contained an activating antibody capable of antibody-dependent cell-mediated cytotoxicity. In certain embodiments, measuring a similar chemiluminescent signal at the time point compared to a control sample is an indication that the sample did not contain an activating antibody capable of antibody-dependent cell-mediated cytotoxicity.

In certain embodiments, this disclosure relates to vectors or cells comprising a vector that encodes a luciferase comprises a nucleic acid that encodes a fluorescent protein followed by internal ribosome entry site sequence followed by a luciferase sequence in operable combination with a controlled promoter. In certain embodiments, the controlled promoter is a tetracycline-controlled cytomegalovirus (CMV) promoter.

In certain embodiments, the effector cells are natural killer cells. In certain embodiments, the ratio of the target cells to the effector cells, used or incubated together in an assay with a sample as described herein, is less than 1:5 such as less than 1:2.5, 1:3, or 1:4 or between 1:1 and 1:2.5, or between 1:1 and 1:3, respectively. In certain embodiments, the ratio of the target cells to the effector cells, used or incubated together in an assay with a sample as described herein, is about 1:2, respectively.

In certain embodiments, the sample is a whole blood sample, plasma, buffy coat, or combination thereof. In certain embodiments, the sample is urine, saliva, semen or vitreous fluid.

In certain embodiments, this disclosure relates to kits comprising target cells and a vector that encodes a luciferase in operable combination with a controlled promoter. In certain embodiments, the kits further comprise a vector that encodes a surface protein. In certain embodiments, the target cells comprise a viral surface protein. In certain embodiments, the kits further comprising an agent that activates the controlled promoter. In certain embodiments, the kits comprise a liquid transfer device such as a syringe, tube, test tube, capillary tube, or pipette.

In certain embodiments, this disclosure relates to kits comprising target cells and the kit further comprises a vector encoding a viral surface protein and a vector encoding a luciferase. In certain embodiments, this disclosure relates to kits comprising target cells comprising a viral surface protein and a vector encoding a luciferase. In certain embodiments, this disclosure relates to kits comprising target cells comprising a viral surface protein and a luciferase inside the cell. In certain embodiments, this disclosure relates to kits comprising target cells comprising a vector that encodes a viral surface protein and a vector that encodes a luciferase in operable combination with a controlled promoter. In certain embodiments, the kit further comprises a luciferin. In certain embodiments, the kit further comprises an agent that activates the controlled promoter.

In certain embodiments, the kit further comprising instructions to mix the target cells and the effector cells in a ratio of less than 1:5 such as less than 1:2.5, 1:3, or 1:4 or between 1:1 and 1:2.5, or between 1:1 and 1:3, respectively. In certain embodiments, the ratio of the target cells to the effector cells is about 1:2, respectively.

In certain embodiments, the disclosure relates to a vector or a cell comprising a vector disclosure herein comprising a nucleic acid disclosed herein. In certain embodiments, the nucleic acid comprises a sequence encoding a fluorescent protein followed by an internal ribosome entry site sequence followed by a sequence encoding a luciferase in operable combination with a controlled promoter. In certain embodiments, the nucleic acid encoding the luciferase comprises SEQ ID NO: 1 or variants thereof including degenerate codons, silent mutations, synonymous mutations, or non-synonymous mutations that do not affect the light producing properties of the luciferase. In certain embodiments, the nucleic acid comprises a sequence encoding an Ebola-virus glycoprotein comprising SEQ ID NO: 3 or variant having 80%, 90%, 95%, 97%, 98%, 99% or greater sequence identity thereto.

BRIEF DESCRIPTION OF THE DRAWINGS

FIG. 1 shows data on the expression of luciferase (Luc) following transient transfection of 293 T cells. 293T cells, at ~70% confluency, were transfected with pcDNA4/TO GFP-IRES-Luc using Lipofectamine 2000. 24 hour later cells were harvested and expression of Luc was analyzed by luciferase assay.

FIG. 2 shows data on the expression of Luc in stably-transfected T-Rex 293 GFP-I-Luc EBOV GP cells after induction with doxycycline. Cells, at ~70% confluency, were induced with 2 μg/ml of doxycycline. 24 hours later cells were analyzed for the expression of luciferase. Luciferase activity is plotted vs target cell number per well with and without doxycycline induction.

FIG. 3A shows data indicating an optimal target:effector cell ratio. Experiments indicated that 1:2 target:effector cell ratio gave least amount of spontaneous cell killing after 4 hours of incubation together.

FIG. 3B shows data on the evaluation of the Ebola ADCC assay with commercially available anti-EBOV GP monoclonal antibodies. % ADCC observed with four commercially available anti-EBOV GP monoclonal antibodies (KZ52, c6D8, c13C6FR1 and h13F6, concentration range: 0.0016-5 μg/ml). Target and effector cells were incubated together, in triplicates, in the presence of different amounts of the antibodies. Four hours later luciferase activity was measured and % ADCC calculated.

FIG. 4 shows the map of original pHAGE PGK-GFP-IRES-Luciferase. GFP-IRES-Luciferase reporter cassette was cut and cloned into plasmid pcDNA4-TO to generate pcDNA4-TO GFP-IRES-LUC.

FIG. 5 illustrates an example of a method of this disclosure. A well with target cells that contain a luciferase (Luc)

and a glycoprotein on the surface are incubated with effector cells. An antibody in the sample binds the glycoprotein on a target cell. Other end of this antibody binds an antibody receptor on the effector cells. The effector cell gets activated causes cytolysis of the target cell. The incubation mixture is centrifuged providing a pellet of cells containing the luciferase (Luc). The supernate is removed and the cells are washed. A luciferin and cell lysing compounds are added to the well and mixed with the washed cells to provide in a chemiluminescent signal. Alternatively, luciferin can be directly mixed with the supernate to produce a chemiluminescent signal.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

In certain embodiments, sequence "identity" refers to the number of exactly matching nucleotides or amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

The term "antibody" is used in the broadest sense and specifically covers monoclonal antibodies (including full length monoclonal antibodies), polyclonal antibodies, multi specific antibodies (e.g., bispecific antibodies), and antibody fragments so long as they exhibit the desired biological activity. Antibodies are proteins which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called complementarity determining regions (CDRs) both in the light chain and the heavy chain variable domains. The more highly conserved portions of the variable domains are called the framework regions (FRs). The variable domains of native heavy and light chains each comprise four FRs, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ, and μ, respectively. Of the various human immunoglobulin classes, human IgG1, IgG2, IgG3 and IgM are known to activate complement; and human IgG1 and IgG3 mediate ADCC more effectively than IgG2 and IgG4.

Papain digestion of antibodies produces two identical antigen binding fragments, called Fab fragments, each with a single antigen binding site, and a residual "Fc" fragment, whose name reflects its ability to crystallize readily. The crystal structure of the human IgG Fc region has been determined (Deisenhofer, Biochemistry 20:2361-2370 (1981)). In human IgG molecules, the Fc region is generated by papain cleavage N-terminal to Cys 226. The Fc region is central to the effector functions of antibodies.

The effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis). Ward and Ghetie, Therapeutic Immunology 2:77-94 (1995).

While binding of an antibody to the requisite antigen has a neutralizing effect that might prevent the binding of a foreign antigen to its endogenous target (e.g. receptor or ligand), binding alone may not remove the foreign antigen. To be efficient in removing foreign antigens, an antibody should be endowed with both affinity binding to its antigen, and efficient effector functions.

The interaction of antibodies and antibody-antigen complexes with cells of the immune system effects a variety of responses, including antibody-dependent cell-mediated cytotoxicity (ADCC) and complement dependent cytotoxicity (CDC) (reviewed in Daëron, Annu. Rev. Immunol. 15:203-234 (1997); Ward and Ghetie, Therapeutic Immunol. 2:77-94 (1995); as well as Ravetch and Kinet, Annu. Rev. Immunol. 9:457-492 (1991)).

Several antibody effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Because each FcγR subclass is encoded by two or three genes, and alternative RNA spicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (reviewed in Ravetch and Kinet, Annu. Rev. Immunol. 9:457-492 (1991)). For example, in humans, FcγRIIIB is found on neutrophils, whereas FcγRIIIA is found on macrophages, monocytes, natural killer (NK) cells, and a subpopulation of T-cells. Notably, FcγRIIIA is FcR present on NK cells, one of the cell types implicated in ADCC.

As used herein, "antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill, e.g., cause lysis of the target cell with cytotoxins. The primary cells for mediating ADCC, NK cells, primarily express FcγRIII, whereas monocytes primarily express FcγRI, FcγRII and FcγRIII Effector cells for assays include peripheral blood mononuclear cells (PBMC) and Natural Killer (NK) cells. ADCC activity may be assessed in vitro or in vivo, e.g., in an animal model such as disclosed in Clynes et al. PNAS (USA) 95:652-656 (1998).

Examples of human leukocyte effector cells which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

An activating antibody which "mediates antibody-dependent cell-mediated cytotoxicity (ADCC) in the presence of effector cells more effectively" than a control antibody is one which in vitro or in vivo is substantially more effective at mediating ADCC, when the amounts of activating antibody and control antibody used in the assay are essentially the same. The activating antibody is typically from about 1.5 fold to about 100 fold, e.g. from about two fold to about fifty fold, more effective at mediating ADCC than the control antibody.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "a nucleic acid sequence encoding" a specified polypeptide refers to a nucleic acid sequence comprising the coding region of a gene or in other words the nucleic acid sequence which encodes a gene product. The coding region may be present in either a cDNA, synthetic copy or genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "luciferase" refers to luciferin oxidative enzymes that function in bioluminescence or chemiluminescence. Luciferin refers to a compound that emits light due to a reaction with a luciferase. A luciferase may be naturally occurring or a non-naturally occurring variant. Examples include firefly luciferase, Gaussia luciferase, aequorin, Metridia luciferase (MetLuc), Renilla reniformis luciferase, and variants thereof. Firefly luciferase is able to oxidize the substrate luciferin, 2-(6-hydroxy-1,3-benzothiazol-2-yl)-4,5-dihydrothiazole-4-carboxylic acid. The catalytic reaction typically includes ATP and oxygen producing an excited-state oxyluciferin and emits light upon relaxation.

Another example luciferase is RLuc8 has the following sequence MASKVYDPEQRKRMITGPQWWARCKQMNVLDSFINYYDSEKHAENAVIFLHGNATSS YLWRHVVPHIEPVARCIIPDLIGMGKSGKSGNGSYRLL-DHYKYLTAWFELLNLPKKIIFV GHDWGAALAF-HYAYEHQDRIKAIVHMESVVDVIESWDEWPDIEEDI-ALIKSEEGEKMV LENNFFVETVLPSKIMRKLEPEEF-AAYLEPFKEKGEVRRPTLSWPREIPLVKGGKPDVVQ IVRNYNAYLRASDDLPKLFIESDPGEESNAIVEGAK-KFPNTEFVKVKGLHFLQEDAPDEM GKYIKSFVE-RVLKNEQ (SEQ ID NO: 4). See Loening et al., Consensus guided mutagenesis of Renilla luciferase yields enhanced stability and light output. Prot. Eng. Des. Sel. 19, 391-400 (2006). Contemplated variants may have greater than 50, 60, 70, 80, 90, 95, 98 or 99% identity or similarity thereto. Coelenterazine (CTZ) is a substrate luciferin of Renilla reniformis luciferase (Rluc) and Gaussia luciferase (Gluc). Coelenterazine and water-soluble derivatives are known luciferins.

Antibody-Dependent Cell-Mediated Cytotoxicity Assay

Figure 5:
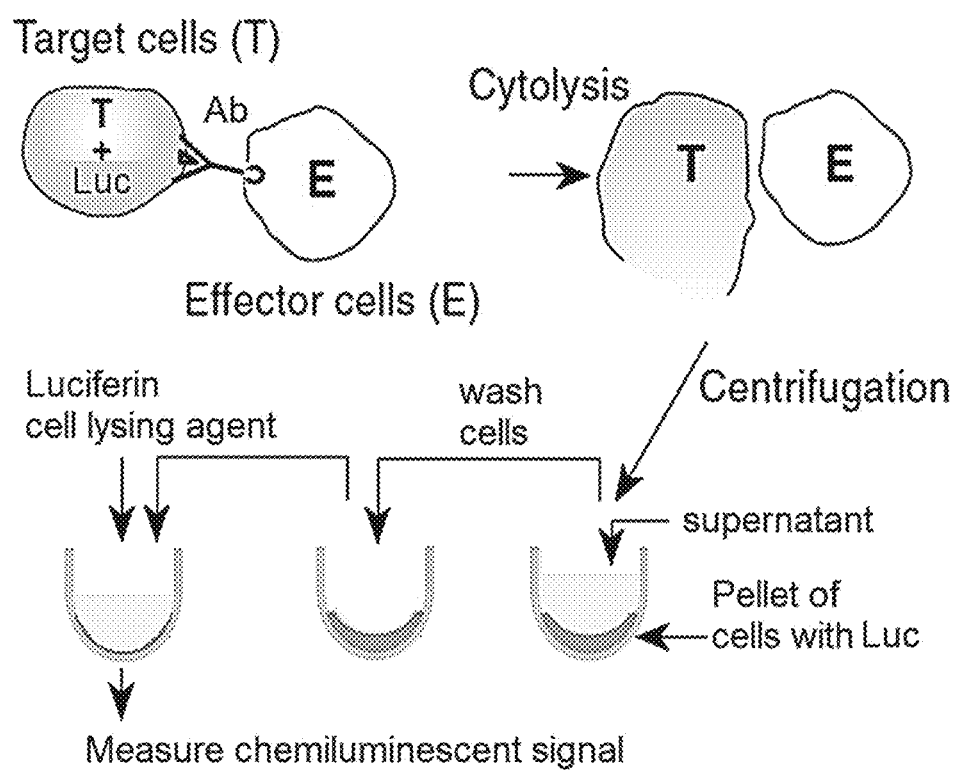

In certain embodiments, this disclosure relates to a non-radioactive, ADCC assay that can accurately measure the ADCC activity of antibodies. ADCC is a mechanism of the immune defense where an antibody binds to an antigen on a target cell, and the same antibody then binds to a receptor on an effector cell, such as a natural killer (NK) cell. The bound NK cell then secretes apoptosis inducing agents breaking up, lysing, and killing a portion of target cell. An illustration of an example assay that is the subject of this disclosure is provided in FIG. 5.

In certain embodiments, the disclosure relates to methods for detecting effector cell activating antibodies in a sample comprising: mixing a sample suspected of containing an activating antibody with target cells and effector cells, wherein the target cells comprise a surface protein and a luciferase inside the target cells, and detecting changes of chemiluminescent signal of the luciferase in the presence of a luciferin in media outside the target cell at a point in time after mixing. In certain embodiments, detecting the presence or absence of a signal or measuring is compared a control sample, e.g., an assay performed with a control antibody with or without the function of inducing antibody-dependent cell-mediated cytotoxicity.

In certain embodiments, this disclosure relates to methods comprising expressing a luciferase in target cells, mixing the target cells with effector cells and a sample containing or suspected of containing an antibody capable of ADCC for an incubation period providing lyses cells and/or a group of luciferase containing target cells not lysed by effector cells, purifying the group of luciferase containing target cells providing purified target cells, lysing the group of purified target cells with a chemical agent providing products of lysis that contain the luciferase, and mixing the products of lysis with a luciferin providing a chemiluminescent signal. The chemiluminescent signal may be measured, quantified, and/or correlated with the amount of target cell lysis by the effector cells or for the presence or absence of an antibody capable of ADCC in the sample.

In certain embodiments, the disclosure relates to methods for detecting effector cell activating antibodies in a sample comprising: a) mixing a sample suspected of containing an activating antibody with target cells and effector cells, wherein the target cells comprise a surface protein and a luciferase inside the target cells, b) incubating the sample for a period of time; c) centrifuging the sample providing a pellet comprising cells and a supernate comprising a liquid sample; d) purifying the pellet of cells from the supernate and lysing the cells in the pellet providing cell lysate and f) mixing the cell lysate with a luciferin and detecting or measuring a chemiluminescent signal of the cell lysate with the luciferin.

In certain embodiments, the disclosure relates to methods for detecting effector cell activating antibodies in a sample comprising: a) mixing a sample suspected of containing an activating antibody with target cells and effector cells, wherein the target cells comprise a surface protein and a luciferase inside the target cells, b) incubating the sample for a period of time; c) centrifuging the sample providing a pellet comprising cells and a supernate comprising a liquid sample; d) purifying the pellet of cells from the supernate and lysing the cells in the pellet providing cell lysate; f) mixing the cell lysate with a luciferin and detecting or measuring a chemiluminescent signal of the cell lysate with the luciferin; and d) correlating the chemiluminescent signal to a presence, absence, or quantity of cell activating antibodies in the sample.

In certain embodiments, the disclosure relates to methods for detecting effector cell activating antibodies in a sample comprising: a) mixing a sample suspected of containing an activating antibody with target cells and effector cells, wherein the target cells comprise a surface protein and a luciferase inside the target cell, b) incubating the sample for a period of time; c) centrifuging the sample providing a pellet comprising cells and a supernate comprising a liquid sample; d) purifying the pellet from the supernate; e) lysing the cells in the pellet providing cell lysate and mixing the cell lysate with a luciferin; and detecting or measuring a chemiluminescent signal of the cell lysate with the luciferin; and f) correlating the chemiluminescent signal at the time point compared to a control sample as an indication that the sample contains an activating antibody capable of antibody-dependent cell-mediated cytotoxicity.

In certain embodiments, detecting the absence of or measuring a decreased chemiluminescent signal at the time point compared to a control sample is an indication that the sample contained an activating antibody capable of antibody-dependent cell-mediated cytotoxicity. In certain embodiments, detecting a signal of or measuring a similar chemiluminescent signal at the time point compared to a control sample is an indication that the sample did not contains an activating antibody capable of antibody-dependent cell-mediated cytotoxicity. In certain embodiments, control sample does not contain an antibody or comprises an antibody that is or is not capable of antibody-dependent cell-mediated cytotoxicity with the effector cells.

In certain embodiments, the disclosure relates to methods for detecting effector cell activating antibodies in a sample comprising: a) mixing a test sample, e.g., sample suspected of containing an activating antibody, with target cells and effector cells, wherein the target cells contain a vector that encodes a viral protein, viral surface protein, or viral glycoprotein, and a vector that encodes a luciferase in operable combination with promoter, or a controlled promoter, wherein the target cells are exposed to a substance that activates the controlled promoter under conditions such that the viral surface protein is expressed and presented on the exterior of the target cell and the luciferase is expressed inside the target cell, b) incubating the sample for a period of time; c) centrifuging the sample providing a pellet comprising cells and a supernate comprising a liquid sample; d) purifying the pellet from the supernate and lysing the cells in the pellet providing cell lysate e) mixing the cell lysate with a luciferin; and f) detecting a chemiluminescent signal of the cell lysate with the luciferin and f) correlating the chemiluminescent signal at the time point compared to a control sample as an indication that the sample contains an activating antibody capable of antibody-dependent cell-mediated cytotoxicity.

In certain embodiments, any of the above methods may exclude lysing the cells in the pellet and instead mixing the cells in the pellet with a cell permeable luciferin such as CycLuc1, 2-(6,7-dihydro-5H-thiazolo[4,5-f]indol-2-yl)-4,5-dihydrothiazole-4-carboxylic acid as reported in Evens et al. Nat Methods. 2014, 11(4): 393-395, or AkaLumine-HCl, 2-(4-(4-(dimethylamino)phenyl)buta-1,3-dien-1-yl)-4,5-dihydrothiazole-4-carboxylic acid, as reported in Kuchimaru et al. Nat Commun. 2016; 7: 11856, or cybLuc, luciferin-6-aminocyclobutane, as reported in Wu et al. Anal Chem. 2017, 89(9): 4808-4816. To the extent that the luciferin is absorbed by the cells and interacts with the luciferase inside the cells, a chemiluminescent signal can be detected or measured and used to make correlations as provided herein.

In certain embodiments, the disclosure relates to methods for detecting effector cell activating antibodies in a sample comprising: a) mixing a sample suspected of containing an activating antibody with target cells and effector cells, wherein the target cells comprise a surface protein and a luciferase inside the target cell, b) incubating the sample for a period of time; c) centrifuging the sample providing a pellet comprising cells and a supernate comprising a liquid sample; and d) mixing the liquid sample with a luciferin and detecting or measuring a chemiluminescent signal of the cell lysate with the luciferin.

In certain embodiments, the disclosure relates to methods for detecting effector cell activating antibodies in a sample comprising: a) mixing a sample suspected of containing an activating antibody with target cells and effector cells, wherein the target cells comprise a surface protein and a luciferase inside the target cell, b) incubating the sample for a period of time; c) centrifuging the sample providing a pellet comprising cells and a supernate comprising a liquid sample; and d) mixing the liquid sample with a luciferin and detecting or measuring a chemiluminescent signal of the cell lysate with the luciferin and e) correlating the chemiluminescent signal at the time point compared to a control sample as an indication that the sample contains an activating antibody capable of antibody-dependent cell-mediated cytotoxicity. In certain embodiments, detecting the signal or measuring an increased chemiluminescent signal at the time point compared to a control sample as an indication that the sample contains an activating antibody capable of antibody-dependent cell-mediated cytotoxicity. In certain embodiments, control sample does not contain an antibody or comprises an antibody that is not capable of antibody-dependent cell-mediated cytotoxicity with the effector cells. In certain embodiments, failing to detect a signal or measuring a decrease chemiluminescent signal at the time point compared to a control sample as an indication that the sample does not contain an activating antibody capable of antibody-dependent cell-mediated cytotoxicity. In certain embodiments, control sample does not contain an antibody or comprises an antibody that is not capable of antibody-dependent cell-mediated cytotoxicity with the effector cells.

In certain embodiments, the disclosure relates to methods for detecting effector cell activating antibodies in a sample comprising: a) mixing a sample suspected of containing an activating antibody with target cells and effector cells, wherein the target cells contain a vector that encodes a viral surface protein and a vector that encodes a luciferase in operable combination with a controlled promoter, wherein the target cells are exposed to a substance that activates the controlled promoter under conditions such that the viral surface protein is expressed and presented on the exterior of the target cell and the luciferase is expressed inside the target cell, b) incubating the sample for a period of time; c) centrifuging the sample providing a pellet comprising cells and a supernate comprising a liquid sample; d) mixing the liquid sample with a luciferin; and f) detecting a chemiluminescent signal of the cell lysate with the luciferin and e) correlating the chemiluminescent signal at the time point compared to a control sample as an indication that the sample contains an activating antibody capable of antibody-dependent cell-mediated cytotoxicity.

EXAMPLES

An Ebola Virus Antibody-Dependent Cell-Mediated Cytotoxicity (Ebola ADCC) Assay

A robust Ebola-specific ADCC assay for use in ongoing trials of Ebola vaccines was developed. The anti-Ebola Zaire (EBOV) GP-specific ADCC assay can reproducibly quantify ADCC activity. Data from infected humans and from the non-human primate model of EVD indicate that fatal outcomes are generally associated with suppressed humoral and cell mediated immune responses, while survivors of EVD mount effective humoral and cell mediated immune responses against Ebola viral antigens. The recombinant vesicular stomatitis virus-based Ebolavirus vaccine rVSV-ZEBOV has been administered as prophylaxis to workers post occupational exposure to Ebola virus, with the intent of raising protective humoral immune responses. These recipients developed strong Ebola-specific antibody responses, and none of them developed EVD. Non-human primates (NHPs) immunized with Ebola virus-like particles developed high-titer ADCC-mediating antibodies that protected the animals against subsequent Ebola virus challenge. A reliable, non-radioactive, Ebola ADCC assay was developed that can accurately measure the ADCC activity of human anti-EBOV GP antibodies.

Generation of Plasmids and Target Cells

An EGFP-IRES-Luciferase reporter cassette derived from plasmid pHAGE PGK-GFP-Luciferase-W (Addgene, Cambridge, Mass.) was cut with Not I and Cla I and then blunted by Klenow Fragment. The blunt fragment was introduced into EcoRV site of plasmid pcDNA4/TO (Invitrogen, Carlsbad, Calif.) to generate plasmid pcDNA4/TO GFP-IRES-Luc. The firefly luciferase (Firefly luciferase of light emitting insects and 4-Coumarate-CoA Ligase (4CL)) is encoded by the following sequence:

```
                                       (SEQ ID NO: 1)
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGCAAGGATATGGGCTCACT
```

```
                                       -continued
GAGACTACATCAGCTATTCTGATTACACCCGAGGGGATGATAAACCGG

GCGCGGTCGGTAAAGTTGTTCCATTTTTTGAAGCGAAGGTTGTGGATCT

GGATACCGGGAAAACGCTGGGCGTTAATCAAAGAGGCGAACTGTGTGTG

AGAGGTCCTATGATTATGTCCGGTTATGTAAACAATCCGGAAGCGACCA

ACGCCTTGATTGACAAGGATGGATGGCTACATTCTGGAGACATAGCTTA

CTGGGACGAAGACGAACACTTCTTCATCGTTGACCGCCTGAAGTCTCTG

ATTAAGTACAAAGGCTATCAGGTGGCTCCCGCTGAATTGGAATCCATCT

TGCTCCAACACCCCAACATCTTCGACGCAGGTGTCGCAGGTCTTCCCGA

CGATGACGCCGGTGAACTTCCCGCCGCCGTTGTTGTTTTGGAGCACGGA

AAGACGATGACGGAAAAAGAGATCGTGGATTACGTCGCCAGTCAAGTAA

CAACCGCGAAAAAGTTGCGCGGAGGAGTTGTGTTTGTGGACGAAGTACC

GAAAGGTCTTACCGGAAAACTCGACGCAAGAAAAATCAGAGAGATCCTC

ATAAAGGCCAAGAAGGGCGGAAAGATCGCCGTGTAA.
```

Codon-optimized EBOV GP gene was synthesized and cloned into pcDNA5-TO (puro) vector at the BamHI-EcoRI cut sites. The plasmid is named pcDNA5-TO(p) Zaire Ebola virus Glycoprotein. The Ebola-virus glycoprotein is encoded by the codon optimized sequence provided below:

```
                                       (SEQ ID NO: 3)
ATGGGCGTCACTGGTATTCTGCAGCTGCCCCGAGATAGGTTCAAGCGGA

CTTCCTTCTTCCTGTGGGTCATCATTCTGTTTCAGCGGACTTTCAGCAT

CCCTCTGGGCGTGATTCACAACTCAACCCTGCAGGTGAGCGACGTGGAT

AAGCTGGTCTGTCGCGACAAACTGAGCTCCACCAATCAGCTGCGATCCG

TGGGACTGAATCTGGAGGGTAACGGAGTGGCAACTGATGTCCCAAGCGC

CACCAAACGGTGGGGTTTAGGTCCGGTGTGCCCCCTAAGGTGGTCAAC

TACGAGGCTGGCGAATGGGCAGAGAATTGCTATAACCTGGAAATCAAGA

AACCTGACGGCAGCGAGTGTCTGCCAGCAGCTCCTGATGGCATTAGGGG

ATTCCCTAGGTGCAGATACGTGCACAAAGTCTCTGGAACCGGGCCATGT

GCCGGAGACTTCGCTTTTCATAAGGAAGGGGCATTCTTTCTGTACGATC

GACTGGCCTCCACCGTGATCTATCGGGGAACCACATTCGCTGAGGGGGT

GGTCGCATTTCTGATTCTGCCCCAGGCTAAGAAAGACTTCTTTTCTAGT

CACCCACTGCGCGAACCCGTGAACGCAACCGAGGACCCCTCAAGCGGCT

ACTATAGTACTACCATCCGATACCAGGCCACAGGTTTCGGCACAAATGA

GACTGAATACCTGTTTGAAGTGGACAACCTGACTTATGTCCAGCTGGAG

AGCAGGTTCACCCCTCAGTTTCTGCTGCAGCTGAACGAAACCATCTATA

CAAGCGGCAAGCGGAGCAATACAACTGGCAAGCTGATTTGGAAAGTGAA

CCCAGAGATCGATACCACAATTGGCGAATGGGCCTTTTGGGAGACAAAG

AAAAATCTGACTCGCAAAATCCGATCTGAGGAACTGAGTTTCACCGTGG

TCTCCAATGGTGCTAAGAACATTAGTGGCCAGTCACCAGCACGCACATC

CTCTGACCCCGGGACTAATACTACCACAGAAGATCACAAGATCATGGCA

TCTGAGAACAGTTCAGCCATGGTGCAGGTCCACAGTCAGGGACGAGAGG

CAGCCGTGTCACATCTGACTACCCTGGCCACTATCTCTACCAGTCCACA
```

-continued

```
GTCTCTGACAACTAAACCTGGACCAGACAATAGTACACATAACACTCCC

GTGTACAAGCTGGATATTAGTGAAGCCACACAGGTCGAGCAGCACCATC

GGAGGACTGACAACGATAGCACCGCTTCCGACACACCATCAGCAACCAC

AGCTGCAGGCCCACCCAAAGCTGAGAATACCAACACATCAAAGAGCACT

GACTTCCTGGACCCCGCCACTACCACATCCCCACAGAATCACTCTGAGA

CAGCTGGAAACAATAACACCCACCATCAGGACACAGGGGAGGAATCTGC

CAGCTCCGGGAAGCTGGGTCTGATCACTAACACCATTGCCGGCGTGGCT

GGACTGATCACTGGCGGAAGACGCACCCGACGGGAAGCAATTGTGAATG

CCCAGCCTAAGTGCAATCCAAACCTGCACTACTGGACTACCCAGGACGA

GGGAGCAGCTATCGGACTGGCTTGGATTCCCTACTTCGGGCCTGCAGCC

GAAGGTATCTATATTGAGGGCCTGATGCATAATCAGGATGGGCTGATCT

GTGGTCTGCGCCAGCTGGCCAACGAAACAACTCAGGCTCTGCAGCTGTT

CCTGAGAGCAACCACAGAGCTGCGCACCTTTTCTATCCTGAACAGGAAG

GCCATTGACTTCCTGCTGCAGAGATGGGGAGGTACATGCCACATCCTGG

GACCAGACTGCTGTATTGAGCCTCATGATTGGACTAAGAATATCACCGA

CAAAATTGATCAGATCATTCACGACTTTGTGGATAAGACACTGCCTGAT

CAGGGTGACAATGATAACTGGTGGACTGGATGGCGACAGTGGATTCCCG

CAGGAATTGGGGTGACCGGCGTCATCATTGCAGTGATCGCCCTGTTTTG

CATTTGTAAATTCGTGTTTTGAGAAT
```

The amino acid sequence of the Ebola-virus glycoprotein is identical to the spike glycoprotein [Zaire ebolavirus] reported as NCBI Reference Sequence: NP_066246.1 provided:

(SEQ ID NO: 2)
```
MGVTGILQLPRDRFKRTSFFLWVIILFQRTFSIPLGVIHNSTLQVSDVD

KLVCRDKLSSTNQLRSVGLNLEGNGVATDVPSATKRWGFRSGVPPKVVN

YEAGEWAENCYNLEIKKPDGSECLPAAPDGIRGFPRCRYVHKVSGTGPC

AGDFAFHKEGAFFLYDRLASTVIYRGTTFAEGVVAFLILPQAKKDFFSS

HPLREPVNATEDPSSGYYSTTIRYQATGFGTNETEYLFEVDNLTYVQLE

SRFTPQFLLQLNETIYTSGKRSNTTGKLIWKVNPEIDTTIGEWAFWETK

KNLTRKIRSEELSFTVVSNGAKNISGQSPARTSSDPGTNTTTEDHKIMA

SENSSAMVQVHSQGREAAVSHLTTLATISTSPQSLTTKPGPDNSTHNTP

VYKLDISEATQVEQHHRRTDNDSTASDTPSATTAAGPPKAENTNTSKST

DFLDPATTTSPQNHSETAGNNNTHHQDTGEESASSGKLGLITNTIAGVA

GLITGGRRTRREAIVNAQPKCNPNLHYWTTQDEGAAIGLAWIPYFGPAA

EGIYIEGLMHNQDGLICGLRQLANETTQALQLFLRATTELRTFSILNRK

AIDFLLQRWGGTCHILGPDCCIEPHDWTKNITDKIDQIIHDFVDKTLPD

QGDNDNWWTGWRQWIPAGIGVTGVIIAVIALFCICKFVF
```

A pcDNA5/TO-puro plasmid was created by replacing hygromycin resistance gene sequence of original pcDNA5/TO vector (Invitrogen) with a puromycin resistance gene. Hygromycin was replaced with puromycin to provide an additional selectable marker, since the target cells are expressing multiple inducible genes. This resistance gene provides robust selection. The puromycin resistance gene was amplified by PCR from pLPCX (Clontech) using CGCACGTGATGACCGAGTACAAGCC (SEQ ID NO: 5) and CGCACGTGTCAGGCACCGGGCTTG (SEQ ID NO: 6) primers. The hygromycin resistance gene was deleted from the original pCDNA5/TO plasmid by digestion with enzyme Pml I, and the puromycin resistance gene inserted in its place. The sequence and orientation of the insert was verified, and the new plasmid named pcDNA5/TO-puro. Codon-optimized EBOV GP gene was placed under a tetracycline-controlled cytomegalovirus (CMV) promoter into plasmid pcDNA5/TO-puro using BamHI and EcoRI sites to generate the plasmid pcDNA5/TO EBOV GP.

To examine GP protein expression, pcDNA5/TO EBOV GP plasmid was transfected into 293T cells, cells were harvested 24 hour later and cell lysates analyzed by western blotting using anti-EBOV GP mAb (4F3) antibody (IBT Bioservices).

Expression of GFP and luciferase reporters was evaluated by transfection of 293T cells with pcDNA4/TO GFP-IRES-Luc. At 24 hours, cells were examined by immunofluorescence microscopy or lysed in Britelite™ Plus luciferase substrate (PerkinElmer, Waltham, Mass.) for examination of luciferase activity as determined using TopCount™ NXT Luminescence Counter (PerkinElmer).

To generate stably-transfected cells expressing EBOV GP and the dual GFP/luciferase reporter, T-REX 293 cells (ThermoFisher Scientific, Waltham, Mass.) were transfected with pcDNA4/TO GFP-IRES-Luc and pcDNA5/TO-puro EBOV GP together using Lipofectamine 2000 (Invitrogen, Carlsbad, Calif.). Forty-eight hours later, the cells were trypsinized and transferred into fresh complete media supplemented with 200 µg/ml Zeocin™ (InvivoGen, San Diego, Calif.) and 0.3 µg/ml puromycin (InvivoGen, San Diego, Calif.) and diluted by serial dilutions to achieve single foci on a culture plate. Single foci were selected and expanded over the coming weeks. Clonal populations growing in individual wells were duplicated and one part was induced with doxycycline (2 µg/ml) (Sigma-Aldrich, St Louis, Mo.) for 24 hours, cells harvested and tested for luciferase, GFP and EBOV GP expression. Clones with high luciferase, GFP and EBOV GP expression were expanded further and used as target cells for the ADCC assay development.

Effector Cells

CD16-176V-NK-92 cell line was obtained from Fox Chase Cancer Center (FCCC). This cells line is retrovirally-transduced to express the 176V high affinity variant of CD16 in the pBMN vector. See ATCC Patent Deposit Designation No. PTA-8836 and U.S. Pat. No. 8,313,943 designated as high affinity variant F176V immunoglobulin gamma Fc region receptor III-A [Precursor]. See table 2, colm 11-14. Parental NK-92 cells, lacking endogenous CD16, and retrovirally transduced to express the 176V variant (GFP-CD16 176V NK-92). See Binyamin et al. Blocking NK cell inhibitory self-recognition promotes antibody-dependent cellular cytotoxicity in a model of anti-lymphoma therapy. J Immunol, 2008 180:6392-6401.

ADCC Assay

Target cells were initially cultured in DMEM media (Gibco, Grand Island, N.Y.) supplemented with 10% Tet-approved FBS (Clontech, Mountain View, Calif.), 1× Glutamax™ (Gibco), 100 IU/ml penicillin and 100 µg/ml streptomycin (both Mediatech, Manassas, Va.), 5 µg/ml blasticidin (InvivoGen, San Diego, Calif.), 200 µg/ml Zeocin™ and 0.3 µg/ml puromycin (complete selection media). Cells were grown in 75 cm² flasks and were induced with 2 µg/ml of doxycycline upon reaching 75% confluence. Twenty-four hours later, cells were harvested by trypsinization, washed twice and re-suspended in MyeloCult™ media (StemCell Technologies) containing 4 µg/ml of doxycycline at a cell density of $5×10^5$ cells/ml. Effector cells were cultured in cell culture flasks in MyeloCult™ media supplemented with 200 IU/ml of recombinant human IL-2 (R&D Systems). On day 3, cells were washed twice and re-suspended in MyeloCult™ media at a cell density of $2×10^6$ cells/ml. The optimal target:effector cell ratio was determined by mixing $5×10^4$ target cells/100 µl/well of 96-well round bottom culture plates (Corning, Corning, N.Y.) with different target:effector cell ratios (1:1, 1:2, 1:5 and 1:10) in a final volume of 200 µl/well. Plates were centrifuged at 300-x-g for 2 min and incubated for 4 hours at 37° C. in a 5% $CO_2$ incubator. Following this incubation, plates were centrifuged again at 300-x-g for 5 minutes, cells washed twice with PBS and re-suspended in 100 µl of MyeloCult™ media. 100 µl of Britelite™ Plus luciferase substrate (PerkinElmer) was added to each well, and cells were lysed by repeated pipetting. 150 µl of the reaction mix from each well was then transferred to the corresponding well of the light protected black assay plates and plates read immediately on a luminometer (TopCount™ NXT Luminescence Counter, PerkinElmer). A target:effector cell ratio of 1:2, giving minimum spontaneous target cell death was selected as optimal ratio for further experiments.

Assay performance was evaluated using four different commercially available anti-EBOV GP monoclonal antibodies (KZ52, c6D8, c13C6FR1 and h13F6, final concentration 0.0016-5 µg/ml) diluted in 50 µl of MyeloCult™ media. $5×10^4$ target cells/100 µl/well were mixed with each antibody, and plates were incubated at 37° C. in 5% $CO_2$ for 10 minutes. Effector cells were then added to each well at $1×10^5$ cells/50 µl/well, and the assay performed as described above. The percent ADCC killing was calculated using the following formula: % ADCC killing: is [((Luciferase units) no antibody control)−((Luciferase units) antibody)×100] divided by ((Luciferase units) no antibody control).

Validation of Reporter Expression and GP Expression

Ebola-Specific ADCC Assay Employing Target And Effector cell lines was developed that is standardized to facilitate reproducible evaluation of Ebola-specific functional activity. Transient transfection of 293 T cells with pcDNA4/TO GFP-IRES-Luc resulted in abundant expression of luciferase and GFP reporters. A feature of the target cells is robust expression of the EBOV GP on the cell surface. EBOV GP expression was first evaluated following transient transfection of 293T cells with pcDNA5/TO-puro EBOV-GP. Western blotting revealed a characteristic EBOV GP band at approximately 130 Kd.

Stable Cell Line Selection

To establish a clonal cell line, T-Rex 293 cells were selected. These cells are adherent and express the Tet repressor protein, allowing regulated expression of reporters and EBOV GP. T-Rex 293 cells were transfected with pcDNA4/TO GFP-IRES-Luc and pcDNA5/TO-puro EBOV GP plasmids, followed by antibiotic selection and single-cell cloning. Clonal populations were examined for luciferase production and for cell surface levels of EBOV GP. Clone T-Rex 293 GFP-I-Luc EBOV GPIS demonstrated the highest luciferase activity and EBOV GP surface expression and was selected for further work. Both luciferase and surface EBOV GP were abundantly expressed by this clonal population.

Development of EBOV GP ADCC Assay

Figure 3A:
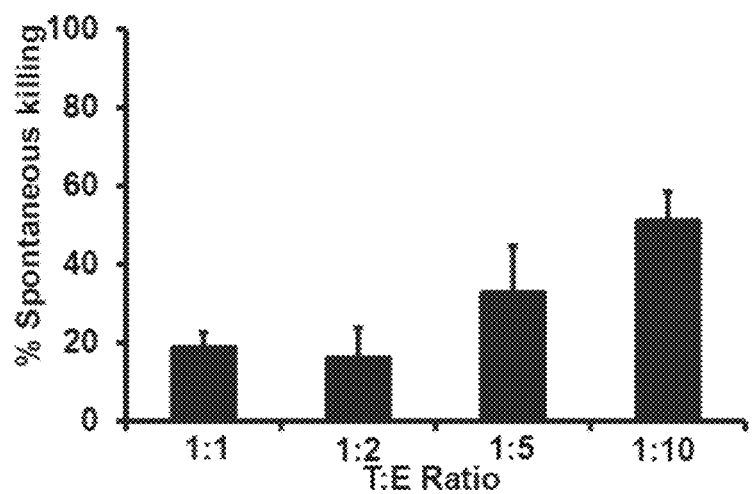
Figure 3B:
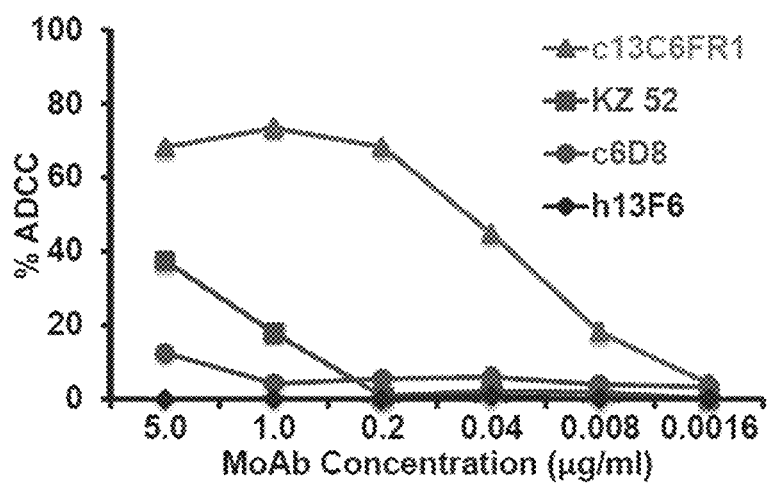
Figure 4:
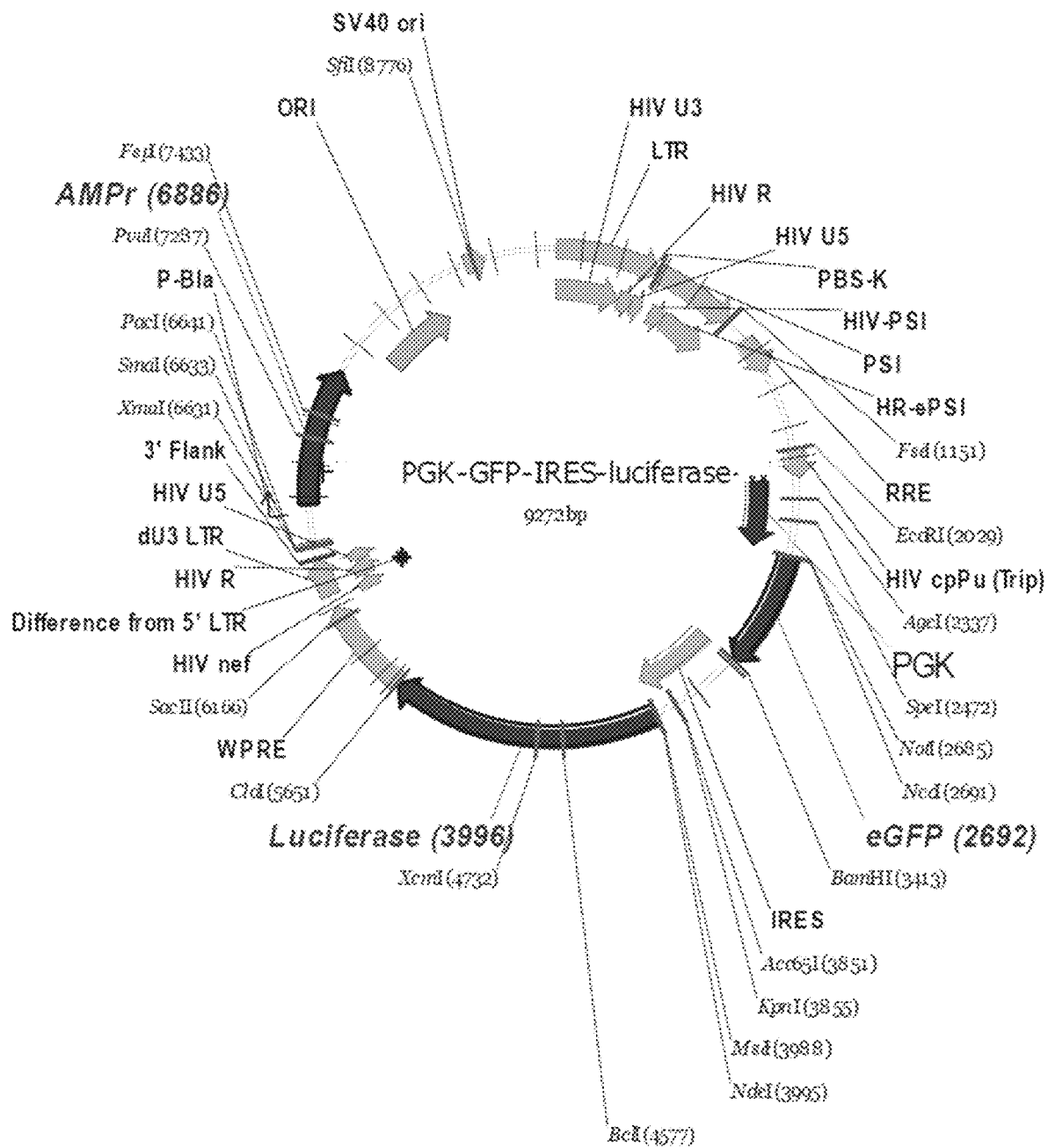

The EBOV GP ADCC assay outlined here utilizes the CD16-176V-NK-92 cell line. Initial mixing experiments were conducted to determine the optimal target:effector cell ratio. EBOV GP target cells were incubated together with effector NK cells for 4 hours. FIG. 3A shows that target: effector ratios of 1:5 and 1:10 resulted in >30% spontaneous killing of targets, while 1:1 and 1:2 ratios produced <20% spontaneous target cell killing. The assay was further tested using a 1:2 ratio to minimize non-specific killing. Next, specific killing using anti-EBOV monoclonal antibodies was evaluated. Four anti-EBOV GP monoclonal antibodies were evaluated, and were found to mediate ADCC to different degrees. c13C6FR1, a human-mouse chimeric, anti-EBOV GP neutralizing monoclonal antibody that is a component of ZMapp and is protective in non-human primate model of EVD, demonstrated the highest level of ADCC (FIG. 3B). KZ52, another human anti-EBOV GP neutralizing monoclonal antibody that failed to impact the course of Ebolavirus infection in non-human primates demonstrated ADCC only at high concentrations. mAbs c6D8 (chimeric, neutralizing) and h13F6 (human, non-neutralizing) that are components of MB-003, did not mediate any significant ADCC killing of the target cells at the concentrations tested (FIG. 3B). Together these results demonstrate the utility of the assay in differentiating antibodies that strongly mediate ADCC killing of the EBOV GP expressing target cells from those that are weakly ADCC positive or are negative.

Ebola ADCC Assay:
Preparation of Culture Media:
  Complete DMEM media:

| | |
|---|---|
| 1. DMEM media | 440 mL |
| 2. Tet system approved, heat inactivated fetal bovine serum | 50 mL |
| 3. Penicillin/Streptomycin | 5 mL |
| 4. Glutamax ™ | 5 mL |
| 5. Puromycin | Final Concentration (0.3 µg/mL) |
| 6. Zeocin ™ | Final Concentration (200 µg/mL) |
| 7. Blasticidin | Final Concentration (5.0 µg/mL) |

Complete MyeloCult™ media

| | |
|---|---|
| 1. MyeloCult ™ H5100 media | 500 mL |
| 2. Recombinant human IL-2 | Final Concentration (200 IU/mL) |

Procedure
Day 1
  1. Culture $4×10^6$ T-Rex-293 GFP-I-Luc EBOV GP target cells in 25 mL of complete DMEM media in a T75 tissue culture flask. Keep the flasks horizontally.
  2. Culture $6×10^6$ CD16-176V-NK-92 effector cells in 25 ml of complete MyeloCult™ media in a T75 tissue culture flask. Keep the flasks vertically.

Day 3
1. Induce the target cells with doxycycline (final concentration: 2 μg/mL) for 24 hours.

Day 4 Harvesting Target cells:
1. Using an aspirating pipet, remove all the medium from the flask.
2. Add 8.0 mL of room temperature 1×PBS. Gently wash the cells and then aspirate all PBS.
3. Add 1.5 mL of trypsin/EDTA solution to the flask and make sure that it touches whole surface covered with the cells.
4. Let the flask sit horizontally for 2 minutes.
5. Detach the cells by gently shaking the flask. Add 18.5 mL of complete DMEM media and transfer the cells into 50 ml tubes.
6. Centrifuge the tubes at 300×g for 10 minutes.
7. Discard the supernatant and re-suspend the cells in 20 ml of MyeloCult™ media.
8. Centrifuge the tubes at 300×g for 10 minutes.
9. Repeat step 7 and 8.
10. Discard the supernatant and re-suspend the target cells in MyeloCult™ media at a density of $0.5 \times 10^6$ cells/mL.

Harvesting Effector Cells:
1. Transfer the CD16-176V-NK-92 effector cells from the flask into 50 ml tubes.
2. Centrifuge the tubes at 300×g for 10 minutes.
3. Discard the supernatant and re-suspend the cells in 20 ml of MyeloCult™ media.
4. Centrifuge the tubes at 300×g for 10 minutes.
5. Repeat step 3 and 4.
6. Discard the supernatant and re-suspend the effector cells in MyeloCult™ media at a density of $2.0 \times 10^6$ cells/ml.

Setting up of the plate and performance of the Ebola ADCC.
1. Add 50 μL of appropriately diluted serum/plasma/antibody in MyeloCult™ media, in triplicates, to the wells of a 96 well U-bottom plate. "No Antibody" control wells receive 50 μL of media, "Target Cells Alone" wells receive 100 μL media while "Effector Cells Alone" wells receive 150 μL of media.
2. Add 100 μL of target cells in each well ($5.0\times10^4$/well) except the "Effector Cells Alone" wells. Mix gently.
3. Incubate the plates for 10 minutes at 37° C. in 5% $CO_2$ incubator.
4. Add 50 μL of effector cells ($1.0\times10^5$/well) to each well except the "Target Cells Alone" wells.
5. Centrifuge the plates at 300×g for 2 minutes.
6. Incubate the plates for 4 hours at 37° C. in a 5% $CO_2$ incubator.
7. Centrifuge the plates at 300×g for 5 min.
8. Discard the supernatant and wash the cells twice with 200 μL/well of PBS.
9. Re-suspend the cells in 100 μl/well of MyeloCult™ media and add 100 μL/well of Britelite™ Plus luciferase substrate (contains luciferin and compounds that facilitate cell lysis).
10. Mix the reaction mix well by pipetting.
11. Transfer 150 μL of the reaction mix from each well to the corresponding wells of a 96 well luciferase assay plate.
12. Read the assay plate in an Illuminometer within 5 minutes.

The invention claimed is:

1. A method of detecting a presence of Ebola-virus antibodies capable of activating effector cells to induce cytolysis of target cells in a sample by correlation with a chemiluminescent signal comprising:
mixing a sample suspected of containing an activating antibody with target cells and effector cells, wherein the target cells comprise an Ebola-virus surface protein and a luciferase inside the target cell, wherein the target cells are stably-transfected clonal cells that express the Ebola virus surface protein and the luciferase, and wherein the effector cells are human natural killer cells;
incubating the sample for a period of time providing a sample mixture;
centrifuging the sample mixture providing a supernatant and a cell pellet having target cells;
mixing the supernatant with a luciferin, wherein the presence of Ebola-virus activating antibodies results in luciferase in the supernatant and results in reaction of luciferin with luciferase providing a chemiluminescent signal;
and detecting the chemiluminescent signal indicating the presence of Ebola-virus antibodies capable of activating effector cells to induce cytolysis of target cells in the sample.

2. The method of claim 1, wherein the ratio of the target cells to the effector cells is less than 1:3.

3. The method of claim 1, wherein the sample is a plasma, serum, or an antibody.

4. The method of claim 1, wherein the Ebola virus surface protein comprises SEQ ID NO: 2.

5. A method for detecting an absence of Ebola-virus antibodies capable of activating effector cells to induce cytolysis of target cells in a sample by correlation with a chemiluminescent signal comprising:
mixing a sample suspected of containing an activating antibody with target cells and effector cells, wherein the target cells comprise an Ebola-virus surface protein and a luciferase inside the target cell, wherein the target cells are stably-transfected clonal cells that express the Ebola virus surface protein and the luciferase, and wherein the effector cells are human natural killer cells;
incubating the sample for a period of time providing a sample mixture;
centrifuging the sample mixture providing a supernatant and a cell pellet having target cells;
purifying the cell pellet from the supernatant and lysing the cells in the pellet providing cell lysate;
mixing the cell lysate with a luciferin; wherein the absence of Ebola-virus activating antibodies results in luciferase in the cell lysate and results in the reaction of luciferin with luciferase providing a chemiluminescent signal; and
detecting the chemiluminescent signal indicating the absence of Ebola-virus antibodies capable of activating effector cells to induce cytolysis of target cells in the sample.

6. The method of claim 5, wherein the ratio of the target cells to the effector cells is less than 1:3.

7. The method of claim 5, wherein the sample is a plasma, serum, or an antibody.

8. The method of claim 5, wherein the Ebola virus surface protein comprises SEQ ID NO: 2.

9. A method of detecting a presence of anti-Ebola virus antibodies capable of mediating antibody-dependent cell-mediated cytotoxicity (ADCC) of target cells, in a sample by correlation with a chemiluminescent signal comprising:
mixing a sample suspected of containing an ADCC-mediating antibody with target cells and effector cells, wherein the target cells comprise an Ebola-virus surface protein and a luciferase inside the target cell, wherein the target cells are stably-transfected clonal cells that express the Ebola virus surface protein and the luciferase, and wherein the effector cells are human natural killer cells;
incubating the sample for a period of time providing a sample mixture;
centrifuging the sample mixture providing a supernatant and a cell pellet having target cells;
mixing the supernatant with a luciferin, wherein the presence of Ebola-virus ADCC-mediating antibodies results in luciferase in the supernatant, and results in the reaction of luciferase with luciferin providing a chemiluminescent signal; and detecting the chemiluminescent signal indicating the presence of Ebola-virus ADCC-mediating antibodies to target cells in the sample.

10. The method of claim 9, wherein the ratio of the target cells to the effector cells is less than 1:3.

11. The method of claim 9, wherein the sample is a plasma, serum, or an antibody.

12. The method of claim 9, wherein the Ebola virus surface protein comprises SEQ ID NO: 2.

13. A method for detecting an absence of Ebola-virus ADCC-mediating antibodies to target cells in a sample by correlation with a chemiluminescent signal comprising:

mixing a sample suspected of containing an activating antibody with target cells and effector cells, wherein the target cells comprise an Ebola-virus surface protein and a luciferase inside the target cell, wherein the target cells are stably-transfected clonal cells that express the Ebola virus surface protein and the luciferase, and wherein the effector cells are human natural killer cells;

incubating the sample for a period of time providing a sample mixture;

centrifuging the sample mixture providing a supernatant and a cell pellet having target cells;

separating the cell pellet from the supernatant and lysing the cells in the pellet providing cell lysate;

mixing the cell lysate with a luciferin, wherein the absence of Ebola-virus ADCC-mediating antibodies results in luciferase in the cell lysate and results in the reaction of luciferin with luciferase providing a chemiluminescent signal; and detecting the chemiluminescent signal indicating the absence of Ebola-virus ADCC-mediating antibodies to target cells in the sample.

14. The method of claim 13, wherein the ratio of the target cells to the effector cells is less than 1:3.

15. The method of claim 13, wherein the sample is a plasma, serum, or an antibody.

16. The method of claim 13, wherein the Ebola virus surface protein comprises SEQ ID NO: 2.

* * * * *

SEQUENCE LISTING

```
<160> NUMBER OF SEQ ID NOS: 6

<210> SEQ ID NO 1
<211> LENGTH: 1653
<212> TYPE: DNA
<213> ORGANISM: Artificial
<220> FEATURE:
<223> OTHER INFORMATION: Synthetic construct

<400> SEQUENCE: 1
atggaagacg ccaaaaacat aaagaaaggc ccggcgccat tctatccgct ggaagatgga     60
accgctggag agcaactgca taaggctatg aagagatacg ccctggttcc tggaacaatt    120
gcttttacag atgcacatat cgaggtggac atcacttacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgggcatt    360
tcgcagccta ccgtggtgtt cgtttccaaa aaggggttgc aaaaaatttt gaacgtgcaa    420
aaaaagctcc caatcatcca aaaaattatt atcatggatt ctaaaacgga ttaccaggga    480
tttcagtcga tgtacacgtt cgtcacatct catctacctc ccggttttaa tgaatacgat    540
tttgtgccag agtccttcga tagggacaag acaattgcac tgatcatgaa ctcctctgga    600
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
```

```
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tccctctct    960 aaggaagtcg gggaagcggt tgccaagagg ttccatctgc caggtatcag gcaaggatat   1020
gggctcactg agactacatc agctattctg attacacccg aggggatga taaaccgggc   1080 gcggtcggta agttgttcc attttttgaa gcgaaggttg tggatctgga taccgggaaa   1140
acgctgggcg ttaatcaaag aggcgaactg tgtgtgagag gtcctatgat tatgtccggt   1200
tatgtaaaca atccggaagc gaccaacgcc ttgattgaca aggatggatg ctacattct   1260 ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gatcgccgtg taa                                1653
```

<210> SEQ ID NO 2  
<211> LENGTH: 676  
<212> TYPE: PRT  
<213> ORGANISM: Artificial  
<220> FEATURE:  
<223> OTHER INFORMATION: Synthetic construct

<400> SEQUENCE: 2

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205
```

```
Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                    245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
        290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
            355                 360                 365

Ala Thr Ile Ser Thr Ser Pro Gln Ser Leu Thr Thr Lys Pro Gly Pro
        370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
610                 615                 620
```

| Gln | Ile | Ile | His | Asp | Phe | Val | Asp | Lys | Thr | Leu | Pro | Asp | Gln | Gly | Asp |
| --- | --- | --- | --- | --- | --- | --- | --- | --- | --- | --- | --- | --- | --- | --- | --- |
| 625 | | | | 630 | | | | | 635 | | | | | 640 | |

| Asn | Asp | Asn | Trp | Trp | Thr | Gly | Trp | Arg | Gln | Trp | Ile | Pro | Ala | Gly | Ile |
| --- | --- | --- | --- | --- | --- | --- | --- | --- | --- | --- | --- | --- | --- | --- | --- |
| | | | 645 | | | | | 650 | | | | | 655 | | |

| Gly | Val | Thr | Gly | Val | Ile | Ile | Ala | Val | Ile | Ala | Leu | Phe | Cys | Ile | Cys |
| --- | --- | --- | --- | --- | --- | --- | --- | --- | --- | --- | --- | --- | --- | --- | --- |
| | | | 660 | | | | 665 | | | | 670 | | | | |

| Lys | Phe | Val | Phe |
| --- | --- | --- | --- |
| | 675 | | |

<210> SEQ ID NO 3
<211> LENGTH: 2035
<212> TYPE: DNA
<213> ORGANISM: Artificial
<220> FEATURE:
<223> OTHER INFORMATION: Synthetic construct

<400> SEQUENCE: 3

| | | | | | |
|---|---|---|---|---|---|
| atgggcgtca | ctggtattct | gcagctgccc | cgagataggt | tcaagcggac | ttccttcttc | 60 |
| ctgtgggtca | tcattctgtt | tcagcggact | ttcagcatcc | ctctgggcgt | gattcacaac | 120 |
| tcaaccctgc | aggtgagcga | cgtggataag | ctggtctgtc | gcgacaaact | gagctccacc | 180 |
| aatcagctgc | gatccgtggg | actgaatctg | gagggtaacg | gagtggcaac | tgatgtccca | 240 |
| agcgccacca | acggtgggg | gtttaggtcc | ggtgtgcccc | ctaaggtggt | caactacgag | 300 |
| gctggcgaat | gggcagagaa | ttgctataac | ctggaaatca | gaaacctga | cggcagcgag | 360 |
| tgtctgccag | cagctcctga | tggcattagg | ggattcccta | ggtgcagata | cgtgcacaaa | 420 |
| gtctctggaa | ccgggccatg | tgccggagac | ttcgcttttc | ataaggaagg | ggcattcttt | 480 |
| ctgtacgatc | gactggcctc | caccgtgatc | tatcgggaa | ccacattcgc | tgaggggtg | 540 |
| gtcgcatttc | tgattctgcc | ccaggctaag | aaagacttct | tttctagtca | cccactgcgc | 600 |
| gaacccgtga | acgcaaccga | ggacccctca | agcggctact | atagtactac | catccgatac | 660 |
| caggccacag | gtttcggcac | aaatgagact | gaatacctgt | ttgaagtgga | caacctgact | 720 |
| tatgtccagc | tggagagcag | gttcacccct | cagtttctgc | tgcagctgaa | cgaaaccatc | 780 |
| tatacaagcg | gcaagcggag | caatacaact | ggcaagctga | tttggaaagt | gaacccagag | 840 |
| atcgatacca | caattggcga | atgggccttt | tgggagacaa | agaaaaatct | gactcgcaaa | 900 |
| atccgatctg | aggaactgag | tttcaccgtg | gtctccaatg | gtgctaagaa | cattagtggc | 960 |
| cagtcaccag | cacgcacatc | tctgacccc | gggactaata | ctaccacaga | agatcacaag | 1020 |
| atcatggcat | ctgagaacag | ttcagccatg | gtgcaggtcc | acagtcaggg | acgagaggca | 1080 |
| gccgtgtcac | atctgactac | cctggccact | atctctacca | gtccacagtc | tctgacaact | 1140 |
| aaacctggac | cagacaatag | tacacataac | actcccgtgt | acaagctgga | tattagtgaa | 1200 |
| gccacacagg | tcgagcagca | ccatcggagg | actgacaacg | atagcaccgc | ttccgacaca | 1260 |
| ccatcagcaa | ccacagctgc | aggcccaccc | aaagctgaga | ataccaacac | atcaaagagc | 1320 |
| actgacttcc | tggaccccgc | cactaccaca | tccccacaga | atcactctga | cagagctgga | 1380 |
| aacaataaca | cccaccatca | ggacacaggg | gaggaatctg | ccagctccgg | gaagctgggt | 1440 |
| ctgatcacta | acaccattgc | cggcgtggct | ggactgatca | ctggcggaag | acgcacccga | 1500 |
| cgggaagcaa | ttgtgaatgc | ccagcctaag | tgcaatccaa | acctgcacta | ctggactacc | 1560 |
| caggacgagg | gagcagctat | cggactggct | tggattccct | acttcgggcc | tgcagccgaa | 1620 |
| ggtatctata | ttgagggcct | gatgcataat | caggatgggc | tgatctgtgg | tctgcgccag | 1680 |
| ctggccaacg | aaacaactca | ggctctgcag | ctgttcctga | gagcaaccac | agagctgcgc | 1740 |

-continued

```
accttttcta tcctgaacag gaaggccatt gacttcctgc tgcagagatg gggaggtaca    1800
tgccacatcc tgggaccaga ctgctgtatt gagcctcatg attggactaa gaatatcacc    1860
gacaaaattg atcagatcat tcacgacttt gtggataaga cactgcctga tcagggtgac    1920
aatgataact ggtggactgg atggcgacag tggattcccg caggaattgg ggtgaccggc    1980
gtcatcattg cagtgatcgc cctgtttttgc atttgtaaat tcgtgttttg agaat        2035
```

<210> SEQ ID NO 4
<211> LENGTH: 311
<212> TYPE: PRT
<213> ORGANISM: Artificial
<220> FEATURE:
<223> OTHER INFORMATION: Synthetic construct

<400> SEQUENCE: 4

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
```

```
<210> SEQ ID NO 5
<211> LENGTH: 25
<212> TYPE: DNA
<213> ORGANISM: Artificial
<220> FEATURE:
<223> OTHER INFORMATION: Synthetic construct

<400> SEQUENCE: 5
cgcacgtgat gaccgagtac aagcc                                              25

<210> SEQ ID NO 6
<211> LENGTH: 24
<212> TYPE: DNA
<213> ORGANISM: Artificial
<220> FEATURE:
<223> OTHER INFORMATION: Synthetic construct

<400> SEQUENCE: 6
cgcacgtgtc aggcaccggg cttg                                               24
```